United States Patent
Martín Molina et al.

(10) Patent No.: US 10,053,709 B2
(45) Date of Patent: Aug. 21, 2018

(54) INSULATOR TO IMPROVE GENE TRANSFER VECTORS

(71) Applicants: FUNDACIÓN PÚBLICA ANDALUZA PROGRESO Y SALUD, Seville (ES); INSTITUTO DE SALUD CARLOS III, Madrid (ES)

(72) Inventors: Francisco Martín Molina, Seville (ES); Karim Benabdellah, Seville (ES); Pilar Muñoz Fernández, Seville (ES); Marién Cobo Pulido, Seville (ES); Alejandra Gutierrez Guerrero, Seville (ES)

(73) Assignees: FUNDACIÓN PÚBLICA ANDALUZA PROGRESO Y SALUD, Seville (ES); INSTITUTO DE SALUD CARLOS III, Madrid (ES)

( * ) Notice: Subject to any disclaimer, the term of this patent is extended or adjusted under 35 U.S.C. 154(b) by 58 days.

(21) Appl. No.: 14/776,008

(22) PCT Filed: Mar. 13, 2014

(86) PCT No.: PCT/EP2014/055027
§ 371 (c)(1),
(2) Date: Sep. 14, 2015

(87) PCT Pub. No.: WO2014/140218
PCT Pub. Date: Sep. 18, 2014

(65) Prior Publication Data
US 2016/0032318 A1 Feb. 4, 2016

(30) Foreign Application Priority Data
Mar. 13, 2013 (EP) ..................................... 13382080

(51) Int. Cl.
*C12N 15/86* (2006.01)
*A61K 48/00* (2006.01)
*C12N 7/00* (2006.01)
*C12P 21/00* (2006.01)

(52) U.S. Cl.
CPC .......... *C12N 15/86* (2013.01); *A61K 48/0066* (2013.01); *C12N 7/00* (2013.01); *C12P 21/00* (2013.01); *C12N 2740/15043* (2013.01); *C12N 2800/95* (2013.01); *C12N 2830/003* (2013.01); *C12N 2830/40* (2013.01); *C12N 2830/46* (2013.01)

(58) Field of Classification Search
CPC ................................ C12N 15/86; C12N 7/00; C12N 2740/15043; C12N 2800/95; C12N 2830/003; C12N 2830/40; C12N 2830/46; A61K 48/0066; C12P 21/00
See application file for complete search history.

(56) References Cited

U.S. PATENT DOCUMENTS

2010/0136616 A1 6/2010 Otte et al.

OTHER PUBLICATIONS

Bell et al., Cell, 98: 387-396, 1999.*
Suttiprapa et al., Transgenic Res., 21(3): Jun. 2012, publically available online Sep. 15, 2011.*
Arumugam P. I. et al., "The 3' Region of the Chicken Hypersensitive Site-4 Insulator Has Properties Similar to Its Core and Is Required for Full Insulator Activity," *PLOS One*, vol. 4, No. 9, pp. 1-15, 2009.
Benabdellah K. et al., "A Chimeric HS4-SAR Insulator (IS2) That Prevents Silencing and Enhances Expression of Lentiviral Vectors in Pluripotent Stem Cells," *PLOS One*, vol. 9, No. 1, pp. 1-15, 2014.
van Drunen C. M. et al., "A bipartite sequence element associated with matrix/scaffold attachment regions," *Nucleic Acids Research*, vol. 27, No. 14, pp. 2924-2930, 1999.
Gutierrez-Guerrero, A. et al., "A Chimeric HS4-SAR insulator (IS2) that prevents silencing and enhances expression in pluripotent stem cells," *Human Gene Therapy*, vol. 24, No. 12, pp. A74-A75, 2013.
International Search Report for PCT/EP2014/055027, dated Jul. 30, 2014.

* cited by examiner

*Primary Examiner* — Thaian N Ton
(74) *Attorney, Agent, or Firm* — McCarter & English, LLP; Jill Ann Mello

(57) ABSTRACT

The present invention solves the problem of providing more efficient barrier insulators to avoid vector silencing and to increase expression in the setting of gene transfer vectors, more particularly in the setting of gene transfer retroviral vectors. In this sense, the authors of the present invention have developed an improved insulator element, namely element IS2, which comprises the following combination of nucleic acid molecules, namely nucleic acid molecule HS4-650 bp as shown in SEQ ID No 2 and a synthetic S/MAR nucleic acid molecule containing 5 M/SARs recognition signatures (MRS) as shown in SEQ ID no 1.

18 Claims, 13 Drawing Sheets

PSAR2. Conserved MRS of Ψβ[5'] locus(Italic-bold sequences), beta-globin locus (capital underlined sequences) and Igk locus (Capital-bold sequences).

taaataaacttataaattgtgagagaaattaatgaatgtctaagttaatgcagaaacggag*gctcctcatttatttt*tgaact
taaagacttaatattgtgaaggtatactttcttta*ataataagcctgcgcc*caatatgttcaccccaaaaaagctgtttgtta
acttgtcaacctcattt<u>AAAATATATAAGAAA</u>CagcccaaagacAATAACAAaag*AA TAATAAA*AAAGA
<u>AT</u>gaaatatgtaattctttcagagtaaaaatcacacccatgacctggccactgagggcttgatcaattcactttgaatttggc
attaaataccattaaggtatattaactgatttAAAATAAGATATATTC

IS1 (HS4_650PSAR2): HS4_650 sequences + PSAR2 (conserved MRS of Ψβ[5'] locus(Italic-bold), beta globin locus (capital underline) and Igk locus (Capital-bold).

aagatct<u>gctcacggggacagccccccccaaagcccccagggatgtaattacgtccctccccgctagggggcagcagcg</u>
<u>agccgcccggggctccgctccggtccggcgctcccccgcatcccgagccggcagcgtgcggggacagcccgggcacgg</u>
<u>ggaaggtggcacgggatcgctttcctctgaacgcttctcgctgctctttgagcctgcagacacctggggggatacggggaaa</u>
<u>atgtgtctgagcctgcatgtttgatggtgtctggatgcaagcagaaggggtggaagagcttgcctggagagatacagctgg</u>
gtcagtaggactgggacaggcagctggagaattgccatgtagatgttcatacaatcgtcaaatcatgaaggctggaaaagc
cctccaagatccccaagaccaaccccaacccacccaccgtgcccactggccatgtccctcagtgccacatccccacagttct
tcatcacctccagggacggtgaccccccacctccgtgggcagctgtgccactgcagcaccgctctttggagaaggtaaatc
ttgctaaatccagcccgaccctcccctggcacaacgtaaggccattatctctcatccaactccaggacggagtcagtgagaa
tatttaaataaacttataaattgtgagagaaattaatgaatgtctaagttaatgcagaaacggag*gctcctcatttatttt*tg
aacttaaagacttaatattgtgaaggtatactttctta*ataataagcctgcgcc*caatatgttcaccccaaaaaagctgttt
gttaacttgtcaacctcattt<u>AAAATATATAAGAAA</u>CagcccaaagacAATAACAAaag*AATAA TAA*AAAA
<u>GAAT</u>gaaatatgtaattctttcagagtaaaaatcacacccatgacctggccactgagggcttgatcaattcactttgaattt
ggcattaaataccattaaggtatattaactgattttAAAATAAGATATATTC

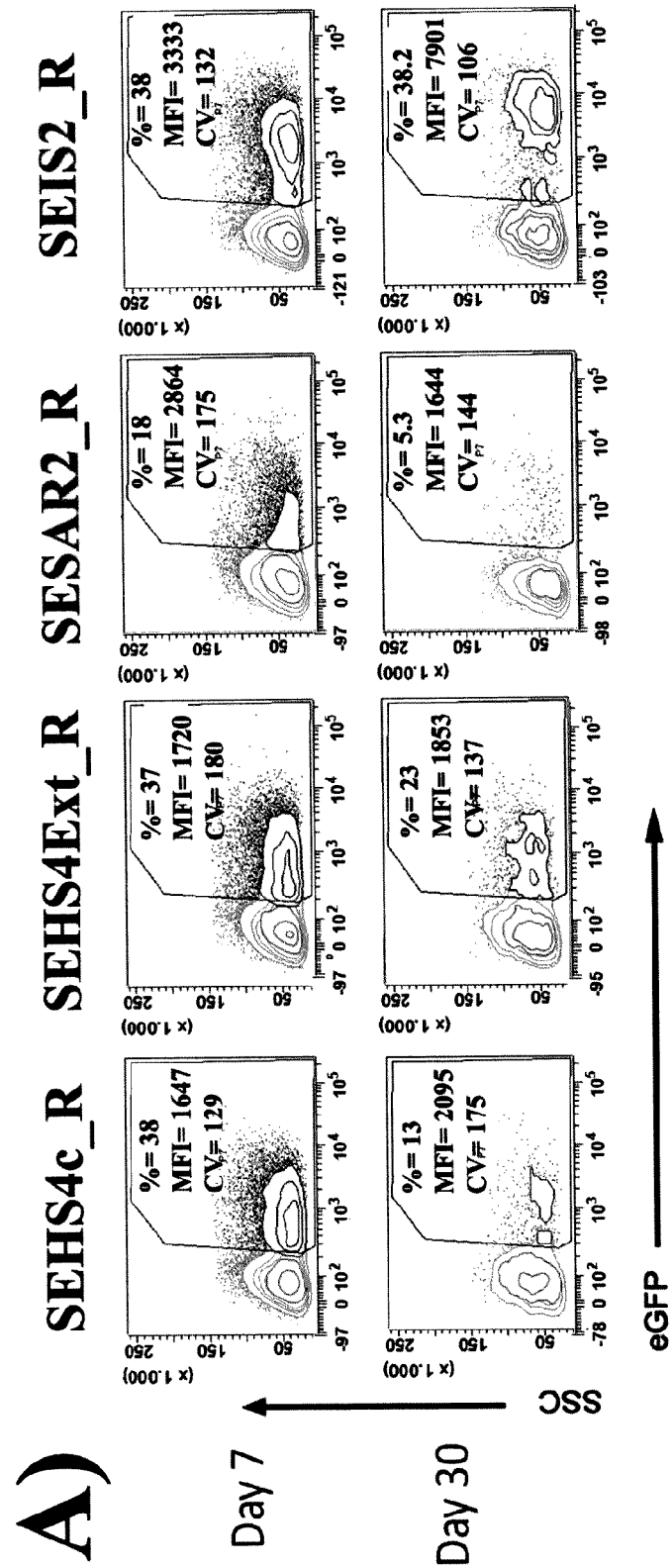
Cont. Figure 3

C)

SEQUENCE LISTING

```
<160> NUMBER OF SEQ ID NOS: 3

<210> SEQ ID NO 1
<211> LENGTH: 367
<212> TYPE: DNA
<213> ORGANISM: Artificial Sequence
<220> FEATURE:
<223> OTHER INFORMATION: Synthetic S/MAR nucleic acid molecule
      containing 5 M /SARs recognition signatures (MRS)
<220> FEATURE:
<221> NAME/KEY: misc_feature
<222> LOCATION: (1)..(367)

<400> SEQUENCE: 1
taaataaact tataaattgt gagagaaatt aatgaatgtc taagttaatg cagaaacgga      60
ggctcctcat ttatttttga acttaaagac ttaatattgt gaaggtatac tttctttaat    120
aataagcctg cgcccaatat gttcacccca aaaaagctgt ttgttaactt gtcaacctca    180
tttaaaatat ataagaaaca gcccaaagac aataacaaaa gaataataaa aaagaatgaa    240
atatgtaatt ctttcagagt aaaaatcaca cccatgacct ggccactgag ggcttgatca    300
attcactttg aatttggcat taaataccat taaggtatat taactgattt taaaataaga    360
tatattc                                                              367

<210> SEQ ID NO 2
<211> LENGTH: 655
<212> TYPE: DNA
<213> ORGANISM: Artificial Sequence
<220> FEATURE:
<223> OTHER INFORMATION: Nucleic acid molecule HS4-650 bp
<220> FEATURE:
<221> NAME/KEY: misc_feature
<222> LOCATION: (1)..(655)

<400> SEQUENCE: 2
aagatctgct cacggggaca gccccccccc aaagccccca gggatgtaat tacgtccctc      60 cccgctagg gggcagcagc gagccgcccg gggctccgct ccgtccggc gctccccg        120 catccccgag ccggcagcgt gcggggacag cccgggcacg gggaaggtgg cacgggatcg    180
ctttcctctg aacgcttctc gctgctcttt gagcctgcag acacctgggg ggatacgggg    240
aaaatgtgtc tgagcctgca tgtttgatgg tgtctggatg caagcagaag gggtggaaga    300
gcttgcctgg agagatacag ctgggtcagt aggactggga caggcagctg gagaattgcc    360
atgtagatgt tcatacaatc gtcaaatcat gaaggctgga aaagccctcc aagatcccca    420
agaccaaccc caacccaccc accgtgccca ctggccatgt ccctcagtgc cacatcccca    480
cagttcttca tcacctccag ggacggtgac ccccccacct ccgtgggcag ctgtgccact    540
gcagcaccgc tctttggaga aggtaaatct tgctaaatcc agcccgaccc tcccctggca    600
```

```
caacgtaagg ccattatctc tcatccaact ccaggacgga gtcagtgaga atatt            655

<210> SEQ ID NO 3
<211> LENGTH: 1022
<212> TYPE: DNA
<213> ORGANISM: Artificial Sequence
<220> FEATURE:
<223> OTHER INFORMATION: IS2
<220> FEATURE:
<221> NAME/KEY: misc_feature
<222> LOCATION: (1)..(1022)

<400> SEQUENCE: 3
aagatctgct cacggggaca gcccccccccc aaagccccca gggatgtaat tacgtccctc      60
ccccgctagg gggcagcagc gagccgcccg gggctccgct ccggtccggc gctcccccg      120 catccccgag ccggcagcgt gcggggacag cccgggcacg gggaaggtgg cacgggatcg      180
ctttcctctg aacgcttctc gctgctcttt gagcctgcag acacctgggg ggatacgggg      240
aaaatgtgtc tgagcctgca tgtttgatgg tgtctggatg caagcagaag gggtggaaga      300
gcttgcctgg agagatacag ctgggtcagt aggactggga caggcagctg gagaattgcc      360
atgtagatgt tcatacaatc gtcaaatcat gaaggctgga aaagccctcc aagatcccca      420
agaccaaccc caacccaccc accgtgccca ctggccatgt ccctcagtgc cacatcccca      480
cagttcttca tcacctccag ggacggtgac cccccacct ccgtgggcag ctgtgccact      540
gcagcaccgc tctttggaga aggtaaatct tgctaaatcc agcccgaccc tcccctggca      600
caacgtaagg ccattatctc tcatccaact ccaggacgga gtcagtgaga atatttaaat      660
aaacttataa attgtgagag aaattaatga atgtctaagt taatgcagaa acggaggctc      720
ctcatttatt tttgaactta aagacttaat attgtgaagg tatactttct ttaataataa      780
gcctgcgccc aatatgttca ccccaaaaaa gctgtttgtt aacttgtcaa cctcatttaa      840
aatatataag aaacagccca aagacaataa caaaagaata ataaaaaaga atgaaatatg      900
taattctttc agagtaaaaa tcacacccat gacctggcca ctgagggctt gatcaattca      960
ctttgaattt ggcattaaat accattaagg tatattaact gattttaaaa taagatatat     1020
tc                                                                    1022
```

INSULATOR TO IMPROVE GENE TRANSFER VECTORS

RELATED APPLICATIONS

This application is a 35 U.S.C. § 371 national stage filing of International Application No. PCT/EP2014/055027, filed on Mar. 13, 2014, which claims priority to European Patent Application No. 13382080.3, filed on Mar. 13, 2013. The entire contents of each of the foregoing applications are incorporated herein by reference.

FIELD OF THE INVENTION

The present invention refers to improved gene transfer vectors for gene therapy. Particularly, the present inventions relates to new DNA sequences capable of enhancing expression and avoid silencing of gene transfer vectors (viral or non-viral). More particularly, the present invention refers to new DNA sequences capable of enhancing expression and avoid silencing of gene transfer vectors (viral or non-viral) in mammalian stem cells.

BACKGROUND OF THE INVENTION

Gene transfer technologies aim to express genes in different cell types in a stable and/or regulated fashion and without affecting physiological expression of the target cell. This technology has demonstrated to be of crucial importance for discovery, protein production and therapeutic use (gene therapy). However, gene transfer vectors (the tools used to transfer the gene into the cells) are confronted with several obstacles such as:

Gene silencing, most vectors loose their expression due to epigenetic modifications.

Variegation. The expression patterns of integrative vectors such as retrovirus vary depending on the site of integration, making it difficult to control the expression of the transgene.

Finally, the integrative vectors affect the expression pattern of the target cell due to the presence of several elements (enhancers, cryptic splice donor and acceptors, poliadenilation sites) that influence the normal expression of genes located near the integration sites.

Thus, gene transfer vectors are hampered with problems at the time of expressing a transgene in a target cell in a stable manner. In this sense, the gene transfer vector backbone seems to be the main player determining stability of transgene expression on target cells. In this regard, some vectors are very prompt to gene silencing due to the presence of viral promoters and/or enhancers. In retroviral vectors, the same elements are also responsible for genotoxicity, mainly due to the activation of oncogenes. In addition, the target cell will also dictate the stability of transgene expression and the potential genotoxicity of the integrative vector. In general, transgene expression on stem and primary cells are more prompt to gene silencing than differentiated and/or immortalized cell lines. In terms of vector genotoxicity, stem cells are the only target cells where serious advert effects (cell transformation) have been observed. Therefore, stable gene transfer in stem cells has been hampered by gene silencing and/or genotoxicity due to vector integration.

There are several ways to reduce silencing and genotoxicity of gene transfer vectors. As already mentioned, vector backbone is a main determinant in this phenomena. In this sense, it has been demonstrated that lentiviral vectors have a safer integration profile compared to gammaretroviral vectors. In the same direction, physiological promoters with weak enhancers are less prompt to oncogen activation that strong viral promoters/enhancers. All these studies point to lentiviruses as the vectors of choice for gene transfer when sustain transgene expression is required. Still, lentiviral vectors do integrate within active genes and this could affect the expression pattern of the target cell. In addition, the expression profile of the lentiviral vectors can also be affected by the integration site.

In order to avoid the deleterious effects of lentiviral vector over the host chromatin and viceversa, different groups have included chromatin insulators (i.e. cHS4) and scaffold (matrix) attachment regions (M/SAR) into the lentiviral backbones. Chromatin insulators form expression boundaries that can have two different activities: 1—Enhancer-blocking, reducing interferences between promoters and enhancers located at different sides of the insulator and 2—barrier activity, preventing gene silencing. S/MAR elements bind to the nuclear matrix and is postulated that this binding defines boundaries of independent chromatin domains that can enhance and/or protect gene expression.

The 1.2 kb chromatin insulator from the chicken β-globin locus control region hypersensitive site 4(cHS4) has been the most widely use insulator in retrovirus vectors. The cHS4 is one of the few insulators that have both, enhancer blocking and barrier activity. When incorporated into the LTR of retroviral vectors, the cHS4 insulator provides uniform gene expression thanks to the enhancer-blocking activity. cHS4 Insulated gamma-retrovirus vectors where also able to avoid gene silencing and to decrease genotoxicity by reducing the activation of oncogenes. However, the incorporation of a large 1.2 kb cHS4 into the retroviral LTR causes a drastic reduction in vector titer.

As an alternative to chromatin insulators, some authors have included S/MAR elements into retroviral vectors either alone or in combination. Insertion of the IFN-SAR into gammaretroviral and lentiviral vectors resulted in improved transgene expression.

However, as discussed previously, transgene silencing and genotoxycity is highly dependent on vector backbone and cell type. Indeed, different (sometimes disappointing) results were obtained when the same insulators were used in different vector backbones or when the same insulated vectors were used in different cell types. For example, initial studies found that gammaretroviral flanked with the cHS4 only prevented silencing in about 30%-70% of the time depending on the expression casset. Especially disappointing were the studies targeting human stem cells, where the beneficial effects can be less obvious.

Therefore, there is a need for more efficient barrier insulators to avoid vector silencing in the setting of retroviral vectors.

SUMMARY OF THE INVENTION

The present invention solves the problem of providing more efficient barrier insulators to avoid vector silencing and to increase expression in the setting of gene transfer vectors, more particularly in the setting of gene transfer retroviral vectors. In this sense, the authors of the present invention have developed an improved insulator element, namely element IS2 (SEQ ID No 3), which comprises the following combination of nucleic acid molecules, namely nucleic acid molecule HS4-650 bp as shown in SEQ ID No 2 and a synthetic S/MAR nucleic acid molecule containing 4 M/SARs recognition signatures (MRS) as shown in SEQ ID No 1. In this regard, the authors of the invention have shown that when this insulator element, namely element IS2, is inserted in the U3 of the 3'LTR region of lentiviral vectors, it is able to enhance expression, avoid silencing and reduce variability of expression in different vectors backbones and different mammalian cells such as stem cell types, including human adult stem cells and embryonic stem cells.

Thus, a first aspect of the present invention refers to an insulator sequence comprising or consisting of SEQ ID No 1, preferably SEQ ID No 1 and SEQ ID No 2, more preferably SEQ ID No 3.

SEQ ID No 3 comprises nucleic acid molecule HS4-650 bp as shown in SEQ ID No 2 and a synthetic S/MAR nucleic acid molecule containing 5 M/SARs recognition signatures (MRS) as shown in SEQ ID no 1. SEQ ID No 3 constitutes the insulator element disclose in the present invention as element IS2.

A second aspect of the present invention refers to a nucleic acid molecule capable of integrating into the genome of a mammalian cell comprising: a) an insulator element, b) regulatory control elements, and c) coding nucleic acid molecules operatively associated with the regulatory elements and capable of expression in the target cell; wherein the insulator element comprises SEQ ID No 1, more preferably SEQ ID No 1 and SEQ ID No 2.

A third aspect of the invention refers to a nucleic acid molecule capable of integrating into the genome of a mammalian cell comprising: a) an insulator element, b) regulatory control elements, and c) coding nucleic acid molecules operatively associated with the regulatory elements and capable of expression in the target cell; wherein the insulator element comprises SEQ ID No 3.

In a preferred embodiment of the second or third aspects of the invention, two identical insulators are located flanking the regulatory and coding sequences, wherein these two identical insulators comprise SEQ ID No 1, preferably SEQ ID No 1 and SEQ ID No 2, more preferably SEQ ID No 3.

A fourth aspect of the invention refers to a vector based on any integrative virus comprising the insulator element of the first aspect of the invention or the nucleic acid molecule as defined in the second or third aspect of the invention. In a preferred embodiment of the fourth aspect of the invention said vector is a lentiviral vector. In a more preferred embodiment of the fourth aspect of the invention the insulator is located at the U3 of the 3'LTR region of the lentiviral vector. Please note that upon reverse transcription and integration, the insulator will be located at both sides of the regulatory and coding sequences.

In a preferred embodiment of the second, third and fourth aspects of the invention, the insulator element is introduced in the anti-sense orientation.

In another preferred embodiment of the second, third and fourth aspects of the invention, the regulatory control element comprises a drug-responsive element. Preferably said regulatory control element comprises a doxycicline-responsive element. More preferably, said regulatory control element comprises a doxycicline-responsive element based on the original TetR repressor.

In yet another preferred embodiment of the second, third and fourth aspects of the invention, the coding nucleic acid molecule is a reporter gene.

In yet another preferred embodiment of the second, third or fourth aspects of the invention, the nucleic acid molecule of the second or third aspect of the invention or the vector of the fourth aspect of the invention comprises two regulatory elements and two coding nucleic acid molecules.

In yet another preferred embodiment, the nucleic acid molecule of the second or third aspect of the invention or the vector of the fourth aspect of the invention comprises two different regulatory elements, one drug-inducible and one constitutive. Preferably, the first regulatory element is regulated by the TetO operon and the second regulatory element expresses the TetR repressor. More preferably, the drug-inducible regulatory element is based on the cytomegalovirus (CMV) promoter and the constitutive regulatory element is based on the Spleen Focus Forming Virus LTR. Still more preferably, the drug-inducible regulatory element is based on any human gene promoter and the constitutive regulatory element is based on the EF1alpha gene promoter.

A fifth aspect of the invention refers to a composition comprising the insulator sequence of the first aspect of the invention or the integrative virus vector of the fourth aspect of the invention or the nucleic acid molecule of the second or third aspects of the invention.

A sixth aspect of the invention refers to a host stem cell comprising the insulator sequence of the first aspect of the invention or the integrative virus vector of the fourth aspect of the invention or the nucleic acid molecule of the second or third aspects of the invention. Preferably, the host cell is a stem cell.

A seventh aspect of the invention refers to the use of the the insulator sequence of the first aspect of the invention or the integrative virus vector of the fourth aspect of the invention or the nucleic acid molecule of the second or third aspects of the invention, for cell marking.

An eighth aspect of the invention refers to the use of the the insulator sequence of the first aspect of the invention or the integrative virus vector of the fourth aspect of the invention or the nucleic acid molecule of the second or third aspects of the invention, for cell genetic manipulation studies.

A ninth aspect of the invention refers to a method for expressing a nucleic acid molecule in a mammalian cell, comprising a) administering to the cell an effective amount of the nucleic acid molecule as defined in the second or third aspects of the invention or the integrative virus vector of the fourth aspect of the invention, and b) expressing the nucleic acid molecule to produce the coding nucleic acid molecule RNA and its encoding polypeptide. Preferably, the host cell is a stem cell.

A tenth aspect of the invention refers to a method for producing a polypeptide in a mammalian cell, comprising a) administering to the cell an effective amount of the nucleic acid molecule as defined in the second or third aspects of the invention or the integrative virus vector of the fourth aspect of the invention, and b) expressing the nucleic acid molecule to produce the coding nucleic acid molecule RNA and its encoding polypeptide.

In a preferred embodiment of the ninth and tenth aspects of the invention, the host cell is a stem cell of adult tissue origin.

In a preferred embodiment of the ninth and tenth aspects of the invention, the host cell is a pluripotent stem cell of adult tissue origin (iPS) or of embryonic origen (ESCs), preferably a non-human embryonic stem cell.

In a preferred embodiment of the ninth aspects of the invention, the host cell is a cell factory for protein production (ie CHOs, HEK free style).

BRIEF DESCRIPTION OF THE DRAWINGS

FIG. 1 illustrates the sequence of the PSAR2 and IS2 elements. A) The PSAR2 is a synthetic M/SAR element designed to contains 4 M/SARs recognition signatures (MRS) as described by van Drunen et al (19). The MRS from the Igk (in capital-bold), the β-globin (capital-underlined) and the ψglobin (italic-bold) where placed overlapping to reduce the length to a minimum. B) The IS2 element where constructed by including the 650 bp HS4 sequence described by Arumugam et al (9) (In gray) upstream of the SAR2 element.

DETAILED DESCRIPTION OF THE INVENTION

Figure 2:
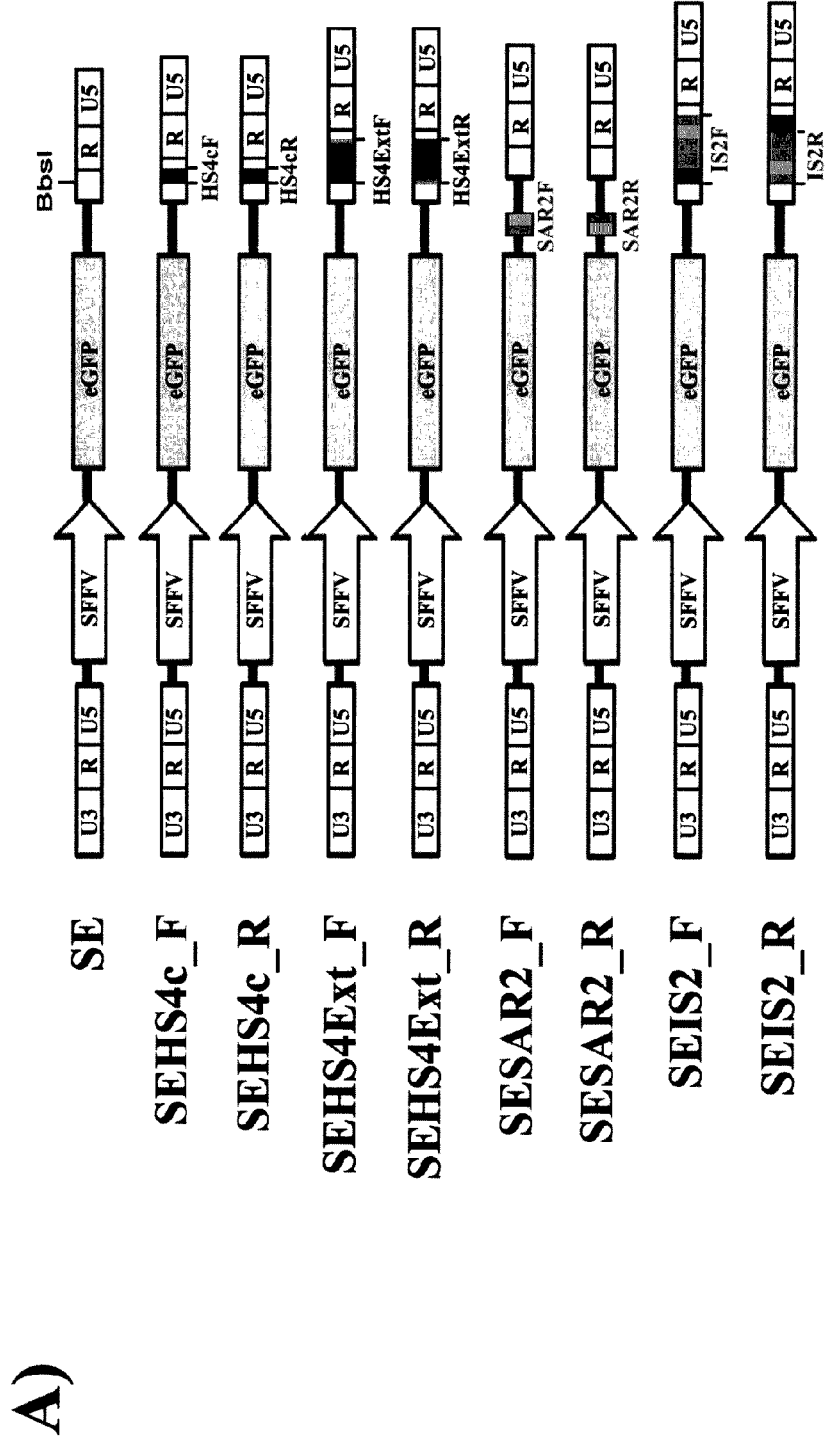
FIG. 2 illustrates how the IS2 element enhances expression and reduces variegation of lentiviral vectors in hESCs (human embryonic stem cells). A) schematic diagrams of the SE lentiviral vector and the modifications including the different Insulators. The 250 bp HS4 core (HS4c) and the 400 pb-HS4 extended (HS4Ext) where used as control of previously describe insulators. All insulators were analyzed in both orientations (F and R). Those containing only the SAR element were inserted between enhanced green fluorescence proteins cDNA and the 3'LTR as previously described. B. FACS plot, showing the percentage (%), Mean Fluorescence Intensity (MFI) and Coefficient of Variation (CV) of GFP positive cells tranduced with different LV carrying the different insulators C. Graphs depicting the Mean fluorescence Intensity (left graph) and coefficient of variation (right graph) of the GFP-positive population of hESCs transduced with the vectors indicated. Values represent mean of at least two separate experiments and the error bar indicates the standard error of the mean.
Figure 2:
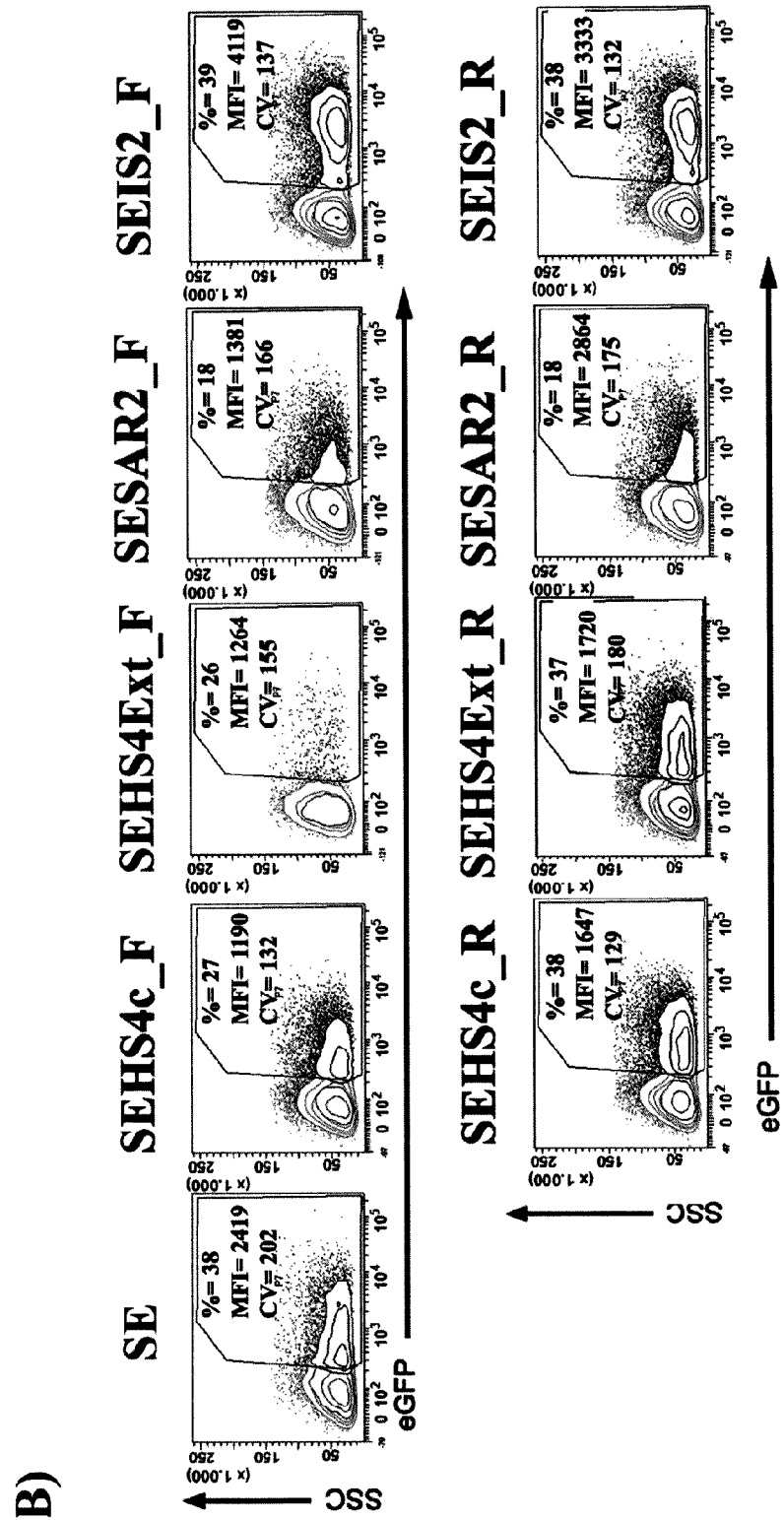
Figure 2:
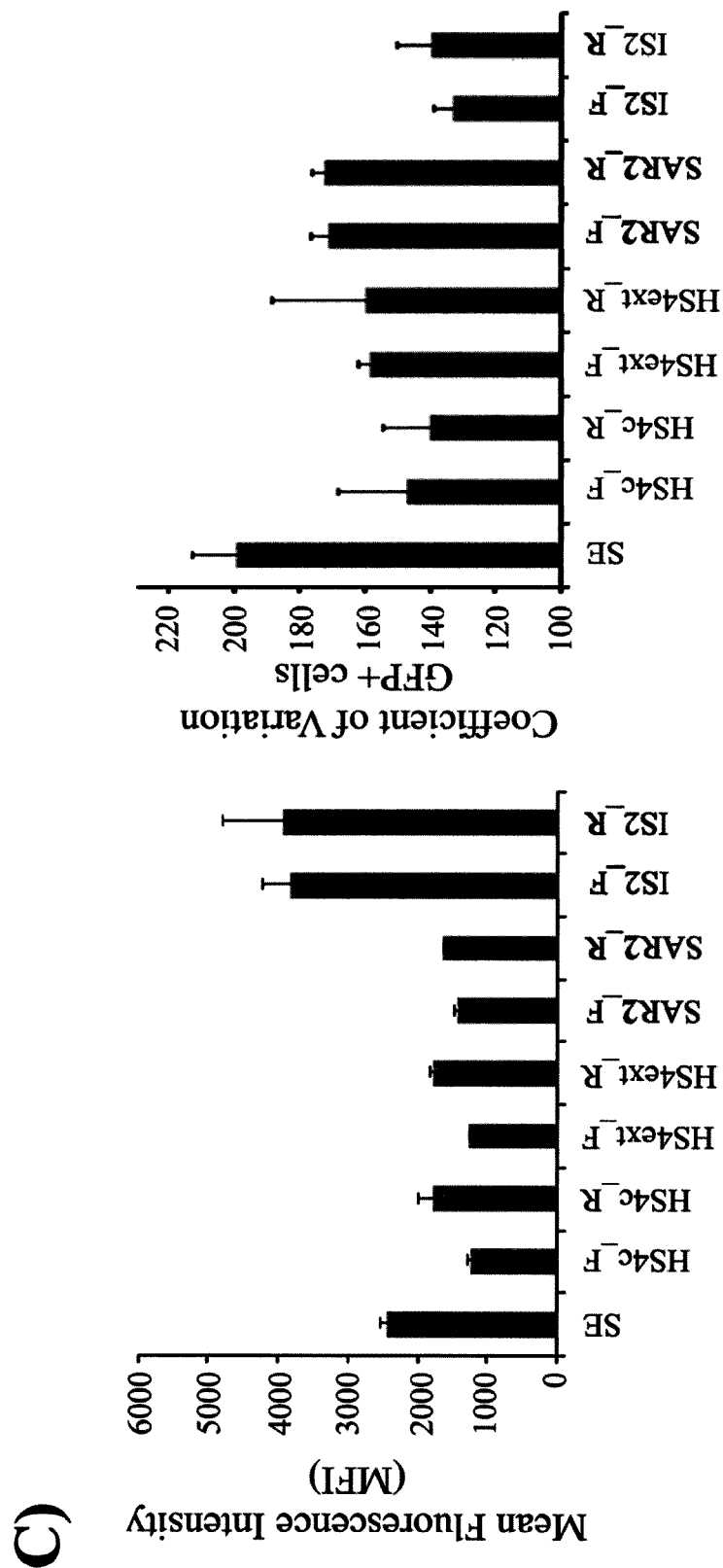

The present invention solves the problem of providing more efficient barrier insulators to avoid vector silencing and to increase expression in the setting of gene transfer vectors, more particularly in the setting of gene transfer retroviral vectors. In this sense, the authors of the present invention have developed an improved insulator element, namely element IS2, which comprises the following combination of nucleic acid molecules, namely nucleic acid molecule HS4-650 bp as shown in SEQ ID No 2 and a synthetic S/MAR nucleic acid molecule containing 4 M/SARs recognition signatures (MRS) as shown in SEQ ID no 1. In this regard, the authors of the invention have shown that when this insulator element, namely element IS2, is inserted in the U3 of the 3'LTR region of lentiviral vectors, it is able to enhance expression, avoid silencing and reduce variability of expression in different vectors backbones and different cell types.

Thus, a first aspect of the present invention refers to an insulator sequence (from hereinafter insulator sequence of the invention) comprising or consisting of SEQ ID No 1, preferably SEQ ID No 1 and SEQ ID No 2, more preferably SEQ ID No 3.

SEQ ID No 3 comprises nucleic acid molecule HS4-650 bp as shown in SEQ ID No 2 and a synthetic S/MAR nucleic acid molecule containing 5 M/SARs recognition signatures (MRS) as shown in SEQ ID no 1. SEQ ID No 3 constitutes the insulator element disclose in the present invention as element IS2.

In the context of the present invention, an insulator element is understood to be a DNA sequence that insulate genes located in one chromatine domain from the effect of enhancers or silencers present in neighbouring domains and viceversa.

The insulator element of the present invention is capable of blocking the silencing action of the regulatory elements placed within its range of action and permits the expression of coding nucleic acid molecules (please note that it is herein understood that the term "coding nucleic acid molecules" includes the term "transgene") in research, protein production and gene therapy in mammalian cells, preferably in embryonic and adult stem cells. Other insulator elements apart from the one disclosed herein, preferably from mammals, having a high level of sequence identity to the insulator elements described in the first and second aspects of the invention can be used in the present invention. Suitable sequences preferably have at least about: 70% identity, at least 80% identity, at least 90% identity, at least 95% identity, at least 96% identity, at least 97% identity, at least 98% identity or most preferably have at least 99% or 99.5% identity to the sequence of an insulator element as described in the first and second aspects above. Identity refers to the similarity of two nucleotide sequences that are aligned so that the highest order match is obtained. Identity is calculated according to methods known in the art. For example, if a nucleotide sequence (called "Sequence A") has 90% identity to a portion of SEQ ID NO 1, then Sequence A will be identical to the referenced portion of SEQ ID NO 1 except that Sequence A may include up to 10 point mutations (such as substitutions with other nucleotides) per each 100 nucleotides of the referenced portion of SEQ ID NO 1.

The invention also includes an insulator element having DNA which in turn has a sequence with sufficient identity to the insulator elements described in the first aspect of the invention to hybridize under stringent hybridization conditions. In this sense, the present invention also includes insulator elements having nucleic acid molecules that hybridize to one or more of the sequences in SEQ ID NO 1-SEQ ID NO 3 or its complementary sequence. Such nucleic acid molecules preferably hybridize under high stringency conditions (see Sambrook et al. Molecular Cloning: A Laboratory Manual, Most Recent Edition, Cold Spring Harbor Laboratory Press, Cold Spring Harbor, N.Y.). High stringency washes have preferably have low salt contents (preferably about 0.2% SSC) and a temperature of about 50-65 C.

Thus, these other insulator elements can be readily inserted in a nucleic acid molecule provided that expression of the coding nucleic acid molecule still occurs.

A second aspect of the present invention refers to a nucleic acid molecule capable of integrating into the genome of a mammalian cell comprising: a) an insulator element, b) regulatory control elements, and c) coding nucleic acid molecules operatively associated with the regulatory elements and capable of expression in the target cell; wherein the insulator element is the insulator sequence defined in the first aspect of the invention or any of its variants. Preferably the insulator sequence comprises or consists of SEQ ID No 1, preferably SEQ ID No 1 and SEQ ID No 2.

A third aspect of the invention refers to a nucleic acid molecule capable of integrating into the genome of a mammalian cell comprising: a) an insulator element, b) regulatory control elements, and c) coding nucleic acid molecules operatively associated with the regulatory elements and capable of expression in the target cell; wherein the insulator element comprises or consists of SEQ ID No 3.

In the context of the present invention, mammalian cells are cells which are derived or isolated from tissue of a mammal. In a preferred embodiment of the inventions these cells are stem cells, preferably pluripotent stem cells of adult tissue origin (iPS) or of embryonic origin (ESCs). In another preferred embodiment of the invention these cells are human mammalian cells of non-embryonic origin (ESCs) or non-human mammalian cells of any origin including embryonic stem cells (ESCs). In another preferred embodiment of the invention these cells are human embryonic stem cells when the nucleic acid molecules described in the present invention are used for therapeutic or diagnostic purposes which are applied to the human embryo and are useful to it.

In the context of the present invention, regulatory control elements are understood to be DNA sequences able to promote the synthesis of RNAs under different conditions.

In the context of the present invention, coding nucleic acid molecules are understood to be DNA sequences that, when transcribed into RNA molecules through the action of the regulatory elements, will give rise to functional proteins or RNAs.

Therefore the nucleic acid molecules described in the second and third aspects of the present invention are constructed from regulatory elements, a coding nucleic acid molecule and insulator sequence/s of the invention. This nucleic acid molecules may be used in vivo or in vitro. Cells transfected or transduced in vitro with this molecules can be used for ex vivo gene therapy or as a research tool or for protein production. This nucleic acid molecules are also useful for gene therapy by transfecting or transducing cells in vivo to express a therapeutic protein. For example, if one were to upregulate the expression of a gene, one could insert the sense sequence into the nucleic acid molecule. If one were to downregulate the expression of the gene, one could insert the antisense sequence into the expression cassette. Techniques for inserting sense and antisense sequences (or fragments of these sequences) would be apparent to those skilled in the art. The nucleic acid molecule described in the second and third aspects of the present invention may be either isolated from a native source (in sense or antisense orientations) or synthesized. It may also be a mutated native or synthetic sequence or a combination of these. Examples of coding nucleic acid molecules to be expressed include 3-globin and GFP expressing reporter genes.

In a preferred embodiment of the second or third aspects of the invention, two identical insulators are located flanking the regulatory and coding sequences, wherein these two identical insulators comprise SEQ ID No 1, preferably SEQ ID No 1 and SEQ ID No 2, more preferably SEQ ID No 3.

In addition, a fourth aspect of the invention refers to a vector based on any integrative virus comprising the insulator sequence of the first aspect of the invention or any of its variants or the nucleic acid molecule as defined in the second or third aspect of the invention. In a preferred embodiment of the fourth aspect of the invention said vector is a lentiviral vector. In a more preferred embodiment of the fourth aspect of the invention the insulator or the nucleic acid molecule is located at the U3 of the 3'LTR region of a lentiviral vector. Please note that upon reverse transcription and integration, the insulator will be located at both sides of the regulatory and coding sequences. Integrative virus vectors containing the nucleic acid molecules of the invention may be administered to mammals, preferably humans, in gene therapy. The polypeptides produced from said vectors may also be administered to mammals, preferably humans.

In the context of the present invention, it is understood that an integrative virus vector is a vector derived from a virus that integrate its genetic material into the host chromosomes and that keep this characteristic once the vector has been developed.

In the context of the present invention, it is understood that the U3 of the 3'LTR region of a lentiviral vector is a sequence that contains the regulatory control elements of the virus, is present only in the 3' end of the viral genome (in the virus particles) and in both ends in the integrated provirus. This sequence is eliminated/mutated from the vectors for safety reasons. In particular in reference to the use of lentiviral vectors in the present invention, the SEQ ID No 1, SEQ ID No 2 or SEQ ID No 3 must be preferentially inserted into the BbsI restriction site of the U3 of the 3'LTR.

In a preferred embodiment of the second, third or fourth aspect of the invention, the insulator element is introduced in the anti-sense orientation.

In another preferred embodiment of the second, third or fourth aspect of the invention, the regulatory control element comprises a drug-responsive element. Preferably said regulatory control element comprises a doxycicline-responsive element. More preferably, said regulatory control element comprises a doxycicline-responsive element based on the original TetR repressor.

In the context of the present invention, it is understood that the original TetR repressor is the product of the tetR gene (the TetR protein) from *Escherichia coli*.

In yet another preferred embodiment of the second, third or fourth aspect of the invention, the coding nucleic acid molecule is a reporter gene.

In yet another preferred embodiment of the second, third or fourth aspect of the invention, the nucleic acid molecule of the second or third aspect of the invention or the vector of the fourth aspect of the invention comprises two regulatory elements and two coding nucleic acid molecules.

In yet another preferred embodiment, the nucleic acid molecule of the second or third aspect of the invention or the vector of the fourth aspect of the invention comprises two different regulatory elements, one drug-inducible and one constitutive. Preferably, the first regulatory element is regulated by the TetO operon and the second regulatory element expresses the TetR repressor. More preferably, the drug-inducible regulatory element is based on the cytomegalovirus (CMV) promoter and the constitutive regulatory element is based on the Spleen Focus Forming Virus LTR. Still more preferably, the drug-inducible regulatory element is based on any human gene promoter and the constitutive regulatory element is based on the EF1alpha gene promoter.

Moreover, the invention also relates to a method of medical treatment of a mammal, preferably a human, by administering to the mammal a nucleic acid molecule of the second or third aspects of the invention or the vector of the fourth aspect of the invention or a cell containing any of these elements. Diseases, such as blood diseases or neural diseases (neurodegenerative), that may be treated are diseases, such as thalassemia or sickle cell anemia that are treated by administering a globin gene. Blood diseases treatable by stem cell transplant include leukemias, myelodysplastic syndromes, stem cell disorders, myeloproliferative disorders, lymphoproliferative disorders phagocyte disorders, inherited metabolic disorders, histiocytic disorders, inherited erythrocyte abnormalities, inherited immune system disorders, inherited platelet abnormalities, plasma cell disorders, and malignancies. Stem cell nerve diseases to be treated by neural stem cell transplantation include diseases resulting in neural cell damage or loss, eg. paralysis, Parkinson's disease, Alzheimer's disease, ALS, multiple sclerosis).

Furthermore, the invention also relates to a mammalian host cell (isolated cell in vitro, a cell in vivo, or a cell treated ex vivo and returned to an in vivo site) comprising the insulator sequence of the first aspect of the invention or the nucleic acid molecule of the second or third aspect of the invention or the vector of the fourth aspect of the invention. In this sense, cells transfected with a nucleic acid molecule as a DNA molecule, or transduced with the nucleic acid molecule as a DNA virus vector, may be used, for example, in bone marrow or cord blood cell transplants according to techniques known in the art. Examples of the use of transduced bone marrow or cord blood cells in transplants are for ex vivo gene therapy of Adenosine deaminase (ADA) deficiency. Other cells which may be transfected or transduced either ex vivo or in vivo include purified stem cells.

In any case such a mammalian cell or mammalian host cell transfected or transduced with a nucleic acid molecule of the second or third aspect of the invention (or variants) or the vector of the fourth aspect of the invention can be useful as research tools to measure levels of expression of the coding nucleic acid molecule and the activity of the polypeptide encoded by the coding nucleic acid molecule. In this sense the nucleic acid molecules of the invention are useful in research to deliver marker genes or antisense RNA to cells.

Thus, a fifth aspect of the invention refers to a mammalian host stem cell comprising the insulator sequence of the first aspect of the invention or any of its variants or the integrative virus vector of the fourth aspect of the invention or the nucleic acid molecule of the second or third aspects of the invention.

A sixth aspect of the invention refers to the use of the insulator sequence of the first aspect of the invention or the integrative virus vector of the fourth aspect of the invention or the nucleic acid molecule of the second or third aspects of the invention, for cell marking.

A seventh aspect of the invention refers to the use of the insulator sequence of the first aspect of the invention or the integrative virus vector of the fourth aspect of the invention or the nucleic acid molecule of the second or third aspects of the invention, for cell genetic manipulation studies.

An eighth aspect of the invention refers to a method for expressing a nucleic acid molecule in a mammalian host cell, comprising a) administering to the cell an effective amount of the nucleic acid molecule as defined in the second or third aspects of the invention or the integrative virus vector of the fourth aspect of the invention, and b) expressing the nucleic acid molecule to produce the coding nucleic acid molecule RNA and its encoding polypeptide. Preferably, the host cell is a stem cell.

A ninth aspect of the invention refers to a method for producing a polypeptide in a mammalian host cell, comprising a) administering to the cell an effective amount of the nucleic acid molecule as defined in the second or third aspects of the invention or the integrative virus vector of the fourth aspect of the invention, and b) expressing the nucleic acid molecule to produce the coding nucleic acid molecule RNA and its encoding polypeptide.

In a preferred embodiment of the eighth and ninth aspects of the invention, the host cell is a stem cell of adult tissue origin.

In a preferred embodiment of the eighth and ninth aspects of the invention, the host cell is a pluripotent stem cell of adult tissue origin (iPS) or of embryonic origen (ESCs), preferably a non-human embryonic stem cell.

In a preferred embodiment of the tenth aspects of the invention, the host cell is a cell factory for protein production (ie CHOs, HEK free style).

A further aspect of the invention refers to a composition comprising the insulator sequence of the first aspect of the invention or the integrative virus vector of the fourth aspect of the invention or the nucleic acid molecule of the second or third aspects of the invention, wherein this composition can be a pharmaceutical composition (from hereinafter pharmaceutical composition of the invention).

The pharmaceutical composition of this invention can be used to treat patients having diseases, disorders or abnormal physical states and could include acceptable carriers or excipients. The pharmaceutical composition of the invention can be administered by ex vivo and in vivo methods such as electroporation, DNA microinjection, liposome DNA delivery, and virus vectors that have RNA or DNA genomes including retrovirus vectors, lentivirus vectors, Adenovirus vectors and Adeno-associated virus (AAV) vectors, Semliki Forest Virus. Derivatives or hybrids of these vectors may also be used.

Dosages to be administered depend on patient needs, on the desired effect and on the chosen route of administration. The expression cassettes may be introduced into the cells or their precursors using ex vivo or in vivo delivery vehicles such as liposomes or DNA or RNA virus vectors. They may also be introduced into these cells using physical techniques such as microinjection or chemical methods such as coprecipitation.

The pharmaceutical composition of the invention can be prepared by known methods for the preparation of pharmaceutically acceptable compositions which can be administered to patients, and such that an effective quantity of the nucleic acid molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

On this basis, the pharmaceutical composition could include an active compound or substance, such as a nucleic acid molecule, in association with one or more pharmaceutically acceptable vehicles or diluents, and contained in buffered solutions with a suitable pH and isosmotic with the physiological fluids. The methods of combining the expression cassettes with the vehicles or combining them with diluents is well known to those skilled in the art. The composition could include a targeting agent for the transport of the active compound to specified sites within the erythroid or other cells.

In addition, the present invention also includes compositions and methods (from hereinafter method of the invention) for providing a coding nucleic acid molecule as defined in the first or second aspect of the invention, to a subject such that expression of the molecule in the cells provides the biological activity of the polypeptide encoded by the coding nucleic acid molecule to those cells. The invention includes methods and compositions for providing a coding nucleic acid molecule to the cells of an individual such that expression of the coding nucleic acid molecule in the cells provides the biological activity or phenotype of the polypeptide encoded by the coding nucleic acid molecule. The method also relates to a method for providing an individual having a disease, disorder or abnormal physical state with a biologically active polypeptide by administering a nucleic acid molecule of the present invention. The amount of polypeptide will vary with the subject's needs. The optimal dosage of vector may be readily determined using empirical techniques, for example by escalating doses.

Various approaches to gene therapy may be used. The invention includes a process for providing a human with a therapeutic polypeptide including: introducing human cells into a human, said human cells having been treated in vitro or ex vivo to insert therein a pharmaceutical composition of the invention of the invention or a vector of the invention, the human cells expressing in vivo in said human a therapeutically effective amount of said therapeutic polypeptide.

The method also relates to a method for producing a stock of recombinant virus by producing virus suitable for gene therapy comprising modified DNA encoding globin. This method preferably involves transfecting cells permissive for virus replication (the virus containing modified globin) and collecting the virus produced.

Finally a further aspect of the invention is an isolated polypeptide produced from a nucleic acid molecule or vector of the invention according to a method of the invention.

The following examples are only meant for illustrative purposes.

EXAMPLES

Example 1. Construction of the Synthetic SAR2 and the IS2 Elements

M/SAR elements are abundant, highly conserved non-coding DNA sequences that play important roles in defining independent chromatin domains and that were originally described by its ability to bind to the nuclear matrix. M/SARs can act by shielding a locus (or transgene) from the effects of the surrounding chromatin and also from the effects of long distance enhancers. These elements have been used to improve transgene expression pattern of retroviral vectors. However, they are very long to combine with other sequences (such as HS4) to improve insulation properties of retroviral vectors without affecting their titer. We have designed a 428 bp synthetic M/SAR element (named SAR2) that contains 4 MRS from 3 different human chromosome regions, the IgK locus, the β-globin locus and the ψβ globin locus (FIG. 1A). In addition, we have constructed another synthetic element (named IS2) combining this SAR2 element with a previously described 650 bp insulator (9) derived from the HS4 insulator (FIG. 1B).

Example 2. The IS2 Element Enhances Transgene Expression Levels of Lentivirus and Reduces the Effect of the Chromatin on Its Expression Pattern LV are the most effective tools for the stable gene delivery, however under some circumstances, transgene expression is either silenced or influenced by sequences neighboring the site of integration. In order to study the effect of the IS2 insulator on LVs gene silencing, we constructed several LVs where this element were inserted in the LV 3'LTR in forward and reverse orientation (FIG. 2B; SIES2_F and SEIS2_R). In order to be able to compare with other insulator previously described, we also inserted the 250 bp HS4 core (HS4c) and the 400 bp HS4 (HS4ext) in identical position (SEHS4_F, SEHS4_R, SEHS4Ext_F and SEHS4Ext_R). In addition we inserted the SAR2 (SESAR2_F and SESAR2_R) just before the 3'LTR to mimic the previously reported configuration of RV incorporating M/SAR elements (11, 12). We first analyzed the transgene expression pattern of the different constructs on human embryonic stem cells (hESCs) (FIGS. 2B and C). We transduced hESCs with the SE LVs containing the different insulators and analyzed the mean fluorescence intensity (MFI) and coefficient of variation (CV) of the eGFP+ cells (FIG. 2B). Interestingly, the IS2 insulator combining the HS4 and PSAR elements render the stronger transgene expression as determine by higher MFI (FIG. 2C left) and the lower variability of expression as determined by the CV (FIG. 2C right). None of the other insulators managed to increase transgene expression levels, but all of them were able to reduce the CV (although to a lower extent that the IS2 element).

Figure 3:
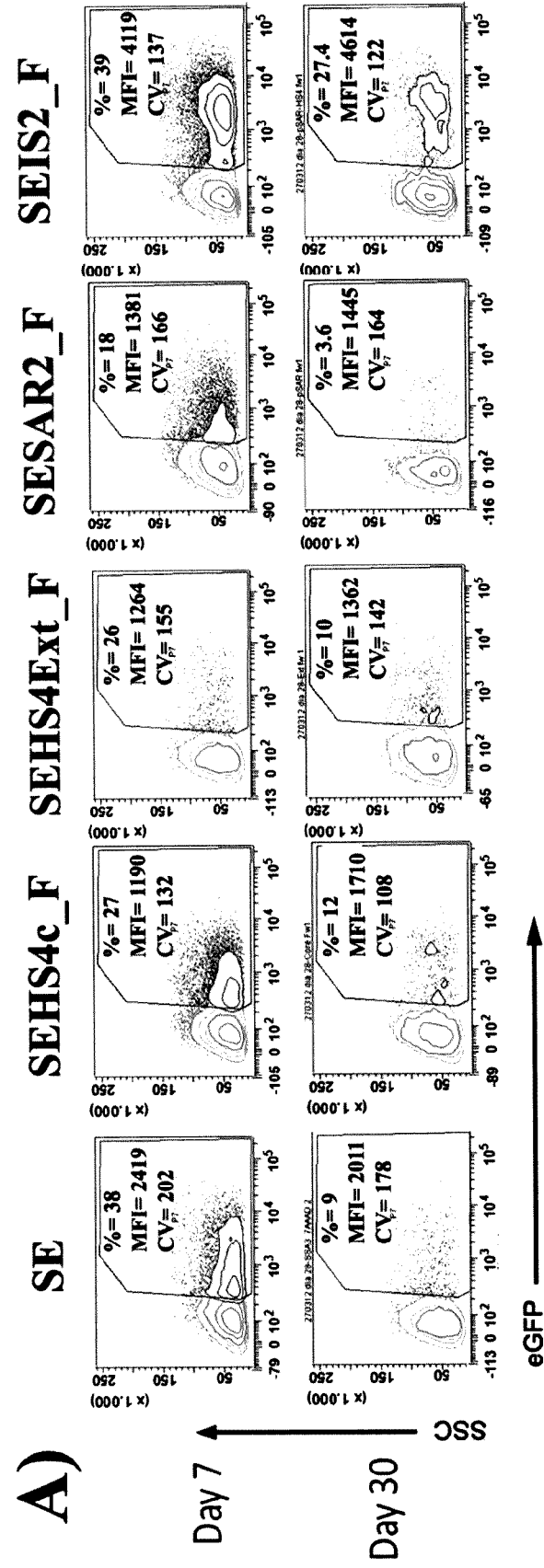
FIG. 3 illustrates how the IS2 element avoids silencing of the SE lentiviral vectors in hESCs. In this sense, hESC cells were transduced at MOI 5 with the different LVs (lentiviral vectors) and analyzed for eGFP expression 7 and 30 days later. A) Representative FACS plots showing the percentage (%), Mean Fluorescence Intensity (MFI) and Coefficient of Variation (CV) of GFP positive cells. B. Graph showing the percentage of eGFP+ cells at day 7 (bars) and 30 (bars) after transduction with the different LVs containing the different insulators. Note the persistence of GFP positive cell in those cells (hESC), tranduced with SEIS2_F and SEIS2_R.
Figure 3:
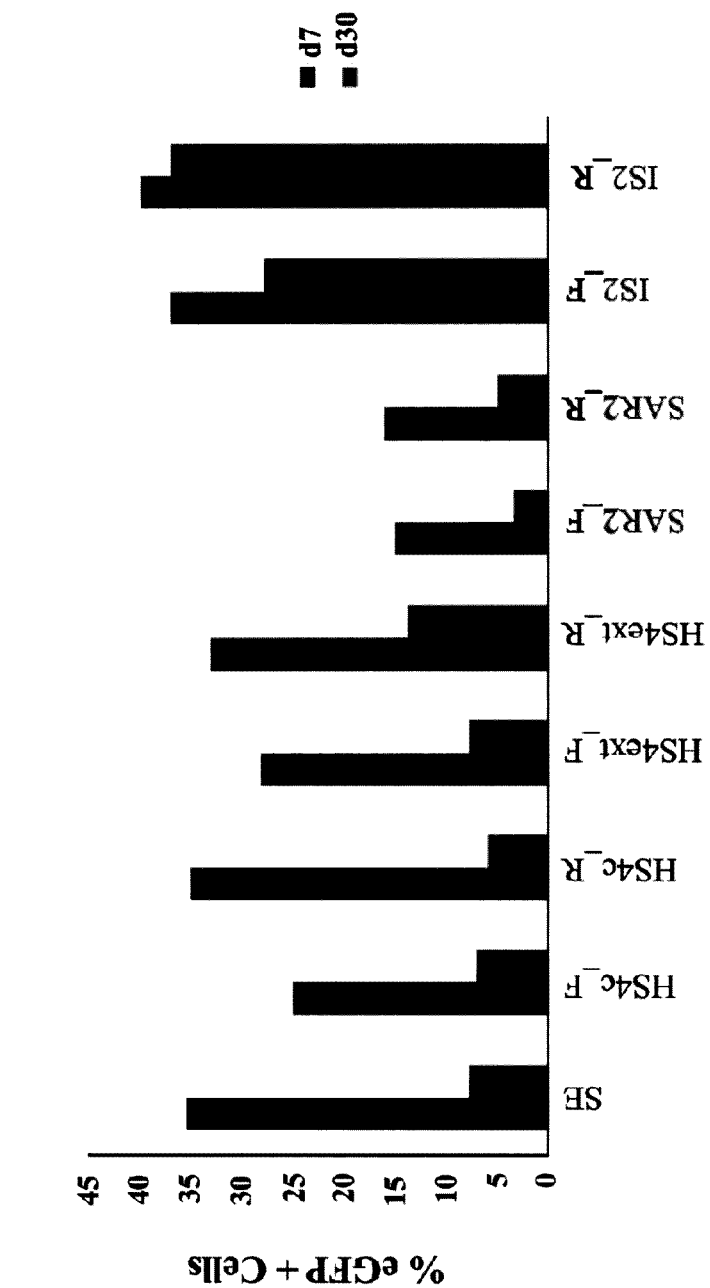

Example 3. Lentivirus Containing the IS2 Insulator are Resistant to Transgene Silencing in Stem Cells To investigate the insulating barrier activity of the SAR2 and IS2 elements, we transduced hESCs with the SEIS2_F, SEIS2_R, SESAR2_F and SESAR2_R LVs and followed eGFP expression for 30 days. The hESCs were also transduced with the SEHS4c_F, SEHS4c_R, SEHS4Ext_f and SEHS4Ext_R LVs In order to compare the barrier activity of the SAR2 and IS2 element with previously described insulators (HS4c and HS4Ext). As can be observed in FIG. 3, while most of the hESCs transduced with the SE LV lost eGFP expression (from 38% to 9%), IS2-containing LVs (SEIS2_R and SEIS2_F) kept eGFP expression almost intact (from 39% to 27% in the forward orientation and from 38% to 38% in the reverse orientation) (FIG. 3 right hand plots). However, neither the SAR2 nor the HS4c elements were able to avoid silencing of the SE vector in this cell line. Only the HS4Ext in the reverse orientation was able to reduced transgene silencing, although to lower degree than the IS2 insulator (FIG. 3B). These experiments show the best performance of the IS2 insulator avoiding transgene silencing compared to the HS4c and to the HS4Ext.

Example 4. IS2 Improved Inducibility and Stability of Expression of Doxycicline-Regulated Lentivirus As mentioned before, the effect of an insulator can vary depending on the vector backbone and the cell type. We therefore analyzed the effect of the IS2 element on two doxycycline-regulated all-in-one LVs (CEST and CEET) and two different cell types (293T and MSCs).

Figure 4:
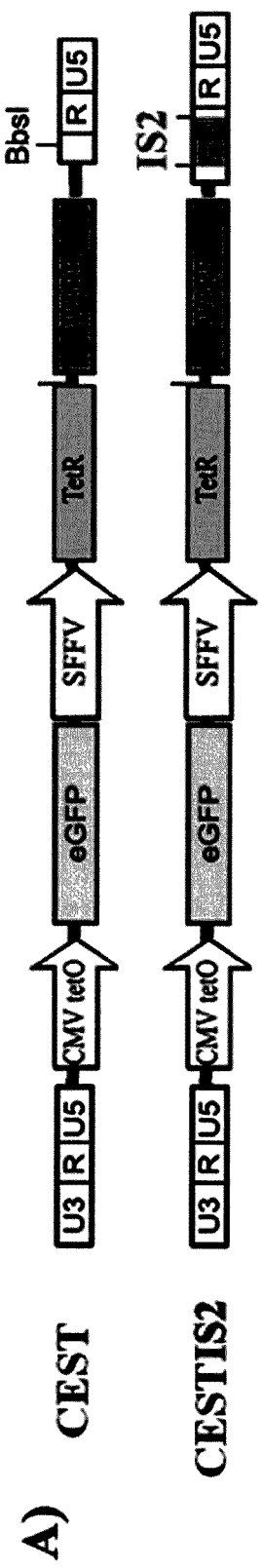
FIG. 4 illustrates how the IS2 element enhances expression and inducibility of doxycycline-regulated LVs. A. Schematic representation of the CEST and CESTIS2 incorporating the IS2 element at the 3'LTR. B. Doxycycline responsiveness of 293T transduced with CEST and CESTIS2 at low MOI (MOI=0.3). The GFP expression of CEST (top plots) and CESTIS2 (bottom plots) is shown in the absence (left plots, −Dox) and presence (right plots, +Dox) of doxycycline. C. Graph showing the fold induction of the CEST and CESTIS2 LVs in 293T cells at increasing MOIs. The average vector genome per cell (v.g.c) of each cell line analyzed is indicated at the top of the bars.
Figure 4:
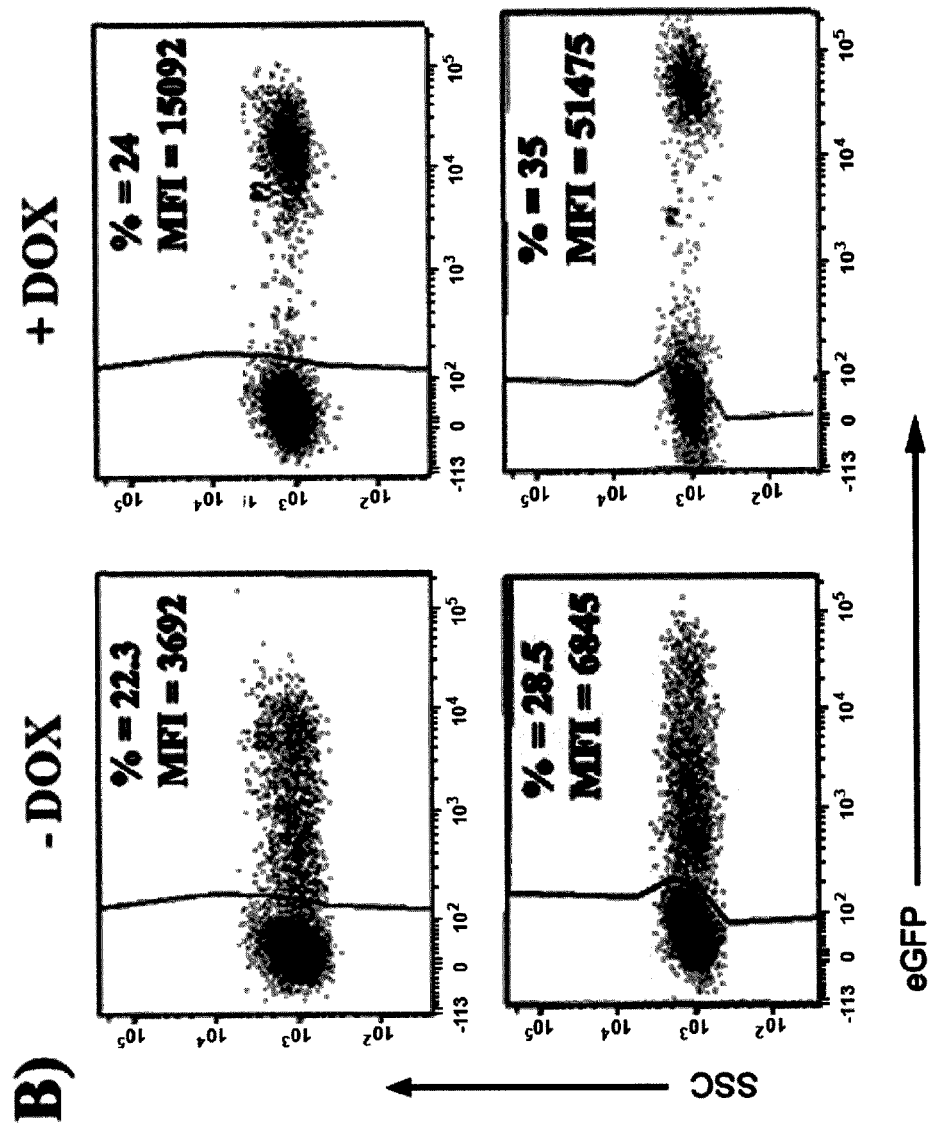
Figure 4:
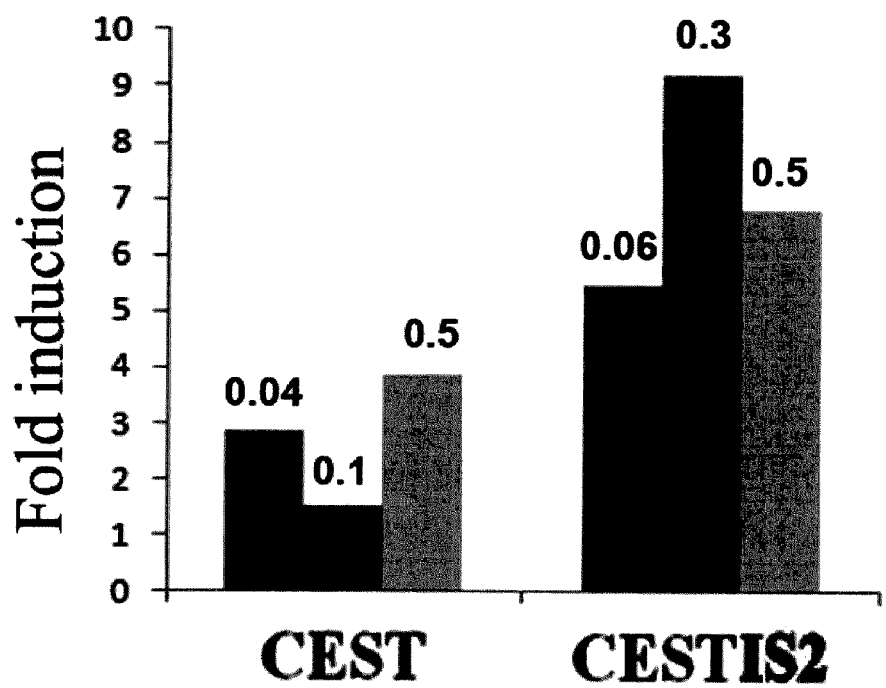

Based on the CEST, a doxycycline-regulated all-in-one LVs expressing the TetR repressor through the SFFV promoter, we constructed the CESTIS2 LV (FIG. 4A). We transduced 293T cells with the CEST and CESTIS2 LVs at different MOIs and analyzed its expression pattern in the presence or absence of doxycycline. As can be observed in FIG. 4B, the IS2 element increases transgene expression levels in the presence of doxycycline (MFI of 51.475 in the CESTIS2 versus 15.092 in the CEST). Interestingly, the CESTIS2 vector presented also higher inducibility (enhancement of expression upon the addition of doxycycline) (FIG. 4C).

Figure 5:
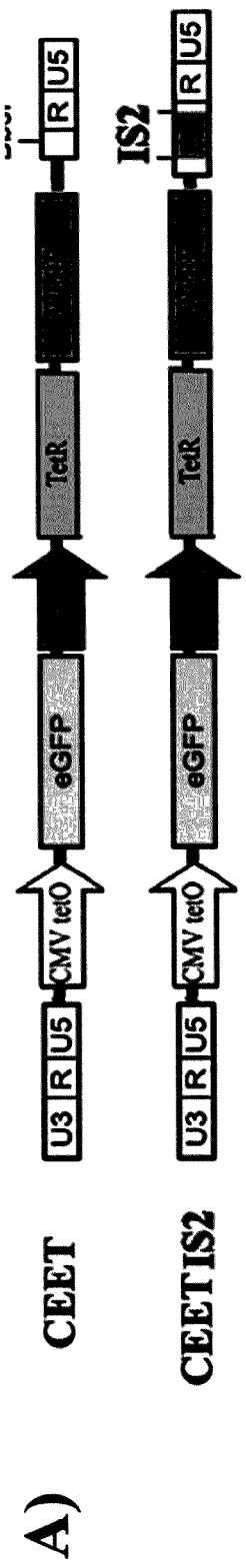
FIG. 5 illustrates how the IS2 element avoids silencing of the CEET lentiviral vectors in hMSC. A). Schematic representation of the CEET and CEETIS2 doxycycline-regulated LVs. B). GFP expression dynamics of CEET- and CEETIS2-transduced MSCs culture for 7 (top) and 27 (bottom) days in the absence (−DOX) or presence (+DOX) of doxycycline. C). Idem after differentiation of transduced cells toward osteocitic (top) and adipocitic (bottom) lineages.
Figure 5:
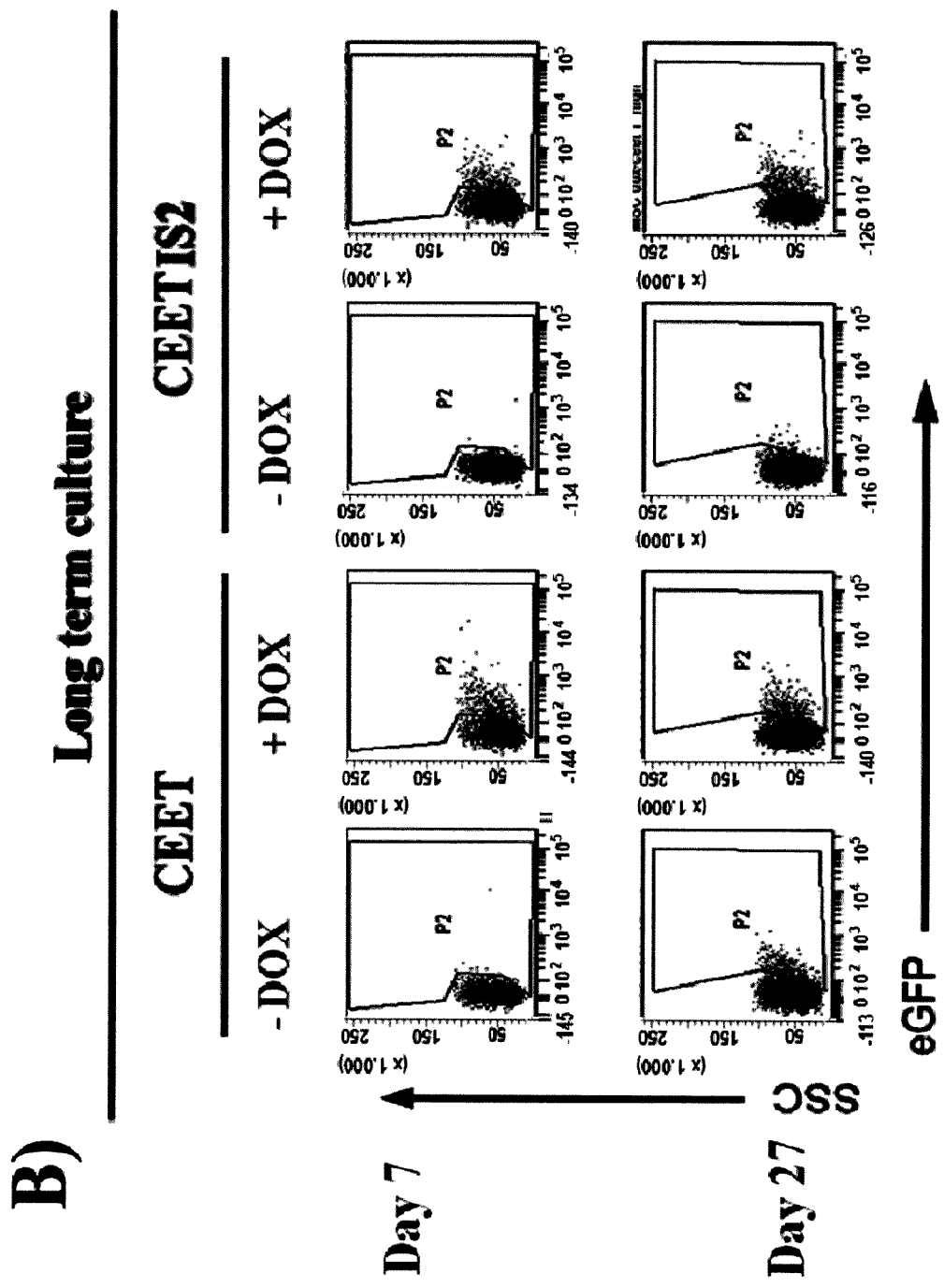
Figure 5:
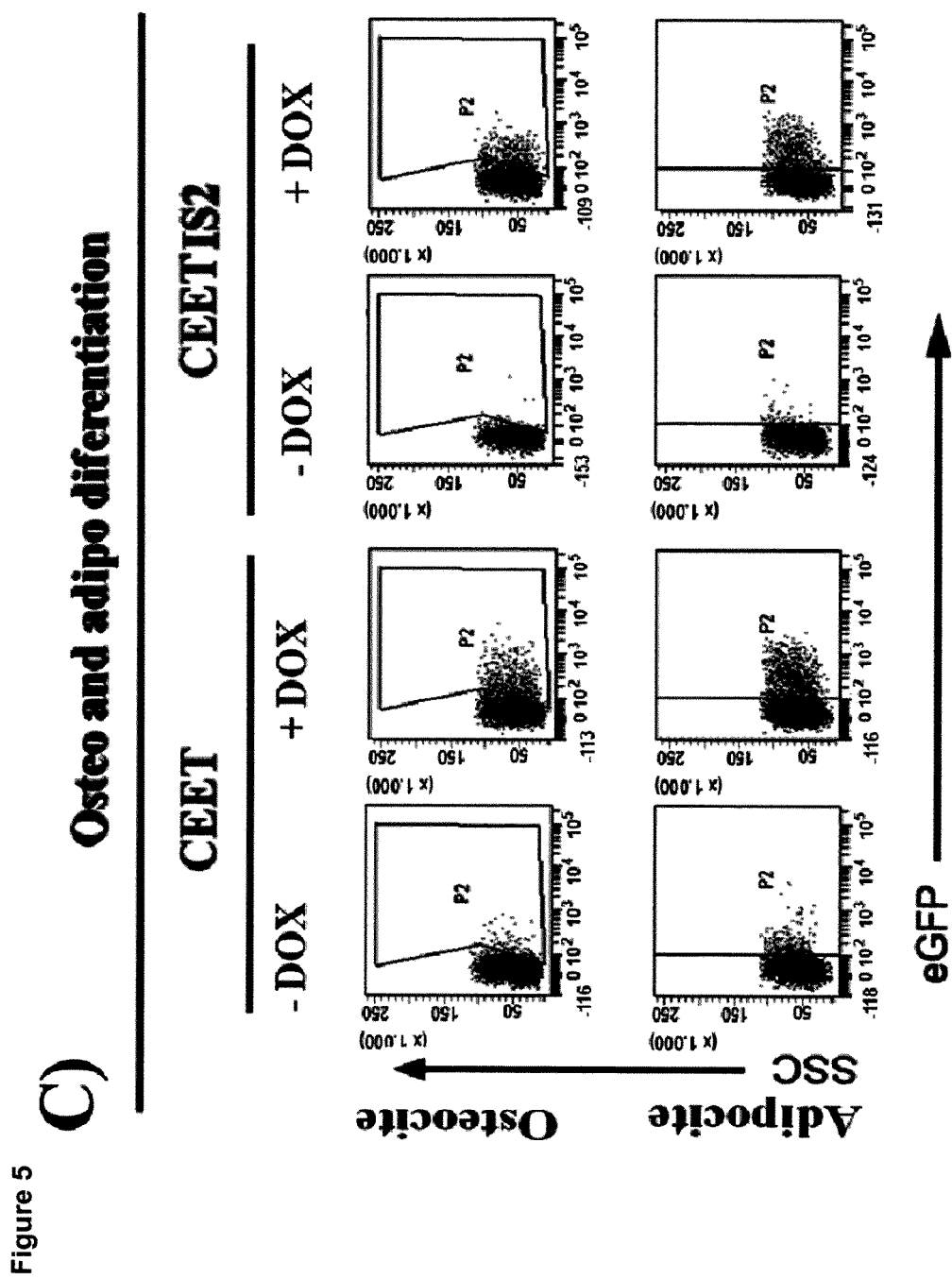

We further test the usefulness of the IS2 element by generating the CEETIS2 from the CEET LV (a doxycycline-regulated all-in-one LVs expressing the TetR repressor through the EF1a promoter) (FIG. 5A). The CEETIS2 and CEET LVs were used to transduce MSCs in order to measure their ability to control eGFP by doxycycline (FIGS. 5B and 5C). We analyzed MSCs under two different conditions: —expansion for 20 days (FIG. 5B) and—differentiation to ostecytes and adipocytes (FIG. 5C). In both culture conditions, the presence of the IS2 element avoid the lost of regulation, minimizing eGFP expression of transduced cells in the absence of doxycycline (compare −DOX plots from CEET transduced-MSCs with −DOX plots from CEETIS2-transduced-MSCs). However in this vector we didn't observed any effect of the IS2 element on either transgene expression or variegation as can be observed in the expression pattern of CEET- and CEETIS2-transduced-MSCs in the presence of doxycycline (FIGS. 5B and 5C, +DOX plots).

The invention claimed is:

1. A nucleic acid molecule comprising a nucleic acid sequence selected from the group consisting of:
   SEQ ID No 3;
   a nucleic acid sequence complementary to the full length of SEQ ID No 3;
   a nucleic acid sequence having at least 95% sequence identity to the full length of SEQ ID No 3; and
   a nucleic acid sequence having at least 95% sequence identity to the full length of a nucleic acid sequence complementary to the full length of SEQ ID No 3.

2. A nucleic acid molecule capable of integrating into the genome of a mammalian cell comprising: a) an insulator element, b) a regulatory control element, and c) a coding nucleic acid molecule operatively associated with the regulatory element and capable of expression in the cell; wherein the insulator element comprises the nucleic acid molecule of claim 1.

3. A viral vector comprising the nucleic acid molecule of claim 2.

4. The viral vector of claim 3, wherein the viral vector is a retroviral vector and wherein the insulator element, the regulatory control element, and the coding nucleic acid molecule operatively associated with the regulatory element are inserted in the U3 of the 3'LTR region of the retroviral vector.

5. The viral vector of claim 4, wherein the retroviral vector is a lentiviral vector.

6. The nucleic acid molecule of claim 2, wherein the insulator element is introduced in the anti-sense orientation.

7. The nucleic acid molecule of claim 2, wherein the regulatory control element comprises a drug-responsive element.

8. The nucleic acid molecule of claim 7, wherein the regulatory control element comprises a doxycycline-responsive element based on the original TetR repressor.

9. The nucleic acid molecule of claim 2, wherein the coding nucleic acid molecule is a reporter gene.

10. The nucleic acid molecule of claim 2, wherein the nucleic acid molecule comprises two regulatory elements and two coding nucleic acid molecules.

11. The nucleic acid molecule of claim 10, wherein the two different regulatory elements are one drug-inducible and one constitutive.

12. A composition comprising a nucleic acid molecule comprising a nucleic acid sequence selected from the group consisting of: SEQ ID No 3;
   a nucleic acid sequence complementary to the full length of SEQ ID No 3;
   a nucleic acid sequence having at least 95% sequence identity to SEQ ID No 3; and
   a nucleic acid sequence having at least 95% sequence identity to a nucleic acid sequence complementary to the full length of SEQ ID No 3.

13. The composition of claim 12, wherein the composition is a pharmaceutical composition further comprising a pharmaceutically acceptable vehicle.

14. An isolated non-human mammalian host stem cell comprising a nucleic acid sequence selected from the group consisting of:
   SEQ ID No 3;
   a nucleic acid sequence complementary to the full length of SEQ ID No 3;
   a nucleic acid molecule having at least 95% sequence identity to the SEQ ID No 3; and
   a nucleic acid sequence complementary to the full length of SEQ ID No 3.

15. The host cell of claim 14, wherein the host cell is a stem cell of embryonic or adult tissue origin.

16. A method for expressing a nucleic acid molecule in a mammalian cell, comprising a) contacting the cell with an effective amount of the nucleic acid molecule of claim 2, and b) expressing the nucleic acid molecule to produce the coding nucleic acid molecule RNA and its corresponding polypeptide.

17. The method of claim 16, wherein the mammalian cell is a stem cell of embryonic or adult tissue origin.

18. The method of claim 16, wherein the mammalian cell is a cell factory for protein production.

* * * * *